(12) United States Patent
Zhou et al.

(10) Patent No.: US 9,926,540 B2
(45) Date of Patent: Mar. 27, 2018

(54) *MYRMECIA INCISA* REISIGL DIACYLGLYCEROL ACYLTRANSFERASE GENE SEQUENCE AND USE THEREOF

(71) Applicant: Shanghai Ocean University, Shanghai (CN)

(72) Inventors: Zhigang Zhou, Shanghai (CN); Haisheng Cao, Shanghai (CN); Fengli Fang, Shanghai (CN)

(73) Assignee: Shanghai Ocean University (CN)

( * ) Notice: Subject to any disclaimer, the term of this patent is extended or adjusted under 35 U.S.C. 154(b) by 0 days.

(21) Appl. No.: 15/021,190

(22) PCT Filed: Jul. 14, 2014

(86) PCT No.: PCT/CN2014/082138
§ 371 (c)(1),
(2) Date: Mar. 10, 2016

(87) PCT Pub. No.: WO2015/085766
PCT Pub. Date: Jun. 18, 2015

(65) Prior Publication Data
US 2016/0222361 A1 Aug. 4, 2016

(30) Foreign Application Priority Data
Dec. 11, 2013 (CN) .......................... 2013 1 0668330

(51) Int. Cl.
| | |
|---|---|
| *C12N 9/10* | (2006.01) |
| *C12P 7/64* | (2006.01) |
| *C07K 14/405* | (2006.01) |
| *C12N 5/14* | (2006.01) |
| *C12N 5/16* | (2006.01) |
| *C12N 15/63* | (2006.01) |

(52) U.S. Cl.
CPC .......... *C12N 9/1029* (2013.01); *C07K 14/405* (2013.01); *C12N 5/14* (2013.01); *C12N 5/16* (2013.01); *C12N 15/63* (2013.01); *C12P 7/6463* (2013.01); *C12Y 203/0102* (2013.01)

(58) Field of Classification Search
None
See application file for complete search history.

(56) References Cited

FOREIGN PATENT DOCUMENTS

| CN | 102943081 A | 2/2013 |
|---|---|---|
| WO | 2009085169 A2 | 7/2009 |

OTHER PUBLICATIONS

Ngo et al. in The Protein Folding Problem and Tertiary Structure Prediction, 1994, Merz et al. (ed.), Birkhauser, Boston, MA, pp. 433 and 492-495.*
Mar. 30, 2010—Identification and characterization of an acyl-CoA:diacylglycerol acyltransferase 2 (DGAT2) gene from the microalga *O. tauri*,—Wagner, M et al.—Plant Physiology and Biochemistry.
2001—Molecular Cloning: A Laboratory Manual—Sambrook and Russell—Cold Spring Harbor Press.
Sep. 30, 2012—The transcriptome pyrosequencing and gene function annotation of the green microalga *Myrmecia incise*—Sihong Chen, et al—Journal of Shanghai Ocean University.
Aug. 31, 2013—Characteristics and function identification of DGAT2 gene—Fang, Fengli et al—Journal of Fisheries of China.
Oct. 10, 2014—International Search Report and Written Opinion—PCT App PCT/CN2014/082138.

* cited by examiner

*Primary Examiner* — Richard G Hutson
(74) *Attorney, Agent, or Firm* — Banner & Witcoff, Ltd.

(57) ABSTRACT

Disclosed are an amino acid sequence of *myrmecia* incise reisigl diacylgycerol acyltransferase, an encoding gene sequence and application thereof. Specifically, based on *myrmecia* incise reisigl transcriptome sequencing data, cloning to obtain full-length cDNA and full-length DNA sequences of a *myrmecia* incise reisigl diacylgycerol acyltransferase gene, and expressing the gene in yeast TAG synthesis defect strain H1246, finding that an encoded protein thereof has a capability for synthesizing a TAG, and using a substrate preference experiment to prove that the encoded protein of the gene tends to C18:1 fatty acid.

7 Claims, 6 Drawing Sheets

MYRMECIA INCISA REISIGL DIACYLGLYCEROL ACYLTRANSFERASE GENE SEQUENCE AND USE THEREOF

CROSS-REFERENCE TO RELATED APPLICATIONS

This application is a U.S. National Stage application under 35 U.S.C. § 371 of International Application PCT/CN2014/082138 (published as WO 2015/085766 A1), filed Jul. 14, 2014, which claims priority to Application CN 201310668330.3, filed Dec. 11, 2013. Benefit of the filing date of each of these prior applications is hereby claimed. Each of these prior applications is hereby incorporated by reference in its entirety.

TECHNICAL FIELD

The present invention relates to genetic engineering, specifically, to a *Myrmecia incisa* Reisigl diacylglycerol acyltransferase gene sequence and use thereof.

BACKGROUND ART

Energy is the foundation of human society development. Facing the global energy crisis, the oil remains in short supply. Bio-energy has become a search focus due to its properties of renewability, and with the unique advantages of no need of food, land and forage, microalgae biodiesel has been attracting increasing attention around the world.

Different species of microalgae have various ability to synthesize triacylglycerol (TAG). It has been revealed that the eukaryotic microalgae (such as green algae or diatom etc.) has higher oil content, which is a promising alga species to produce biodiesel. *Myrmecia incisa* Reisigl H4301 is a single-cell freshwater microalga belonging to Chlorophyta with accumulated amounts of TAG, especially under a nitrogen starvation stress. Therefore, *Myrmecia incisa* can be regarded as a potential algal species for production of biodiesel.

TAG is the major storage form of lipid in plants, and plays an important role in the growth and development of plants. Three TAG synthesizing enzymes have been found: diacylglycerol acyltransferase (DGAT, EC 2.3.1.20), phospholipid: diacylglycerol acyltransferase (PDAT, EC 2.3.1.158), and diacylglycerol transacylase (DGTA). Therein, DGAT, the most important enzyme in TAG synthesis, catalyzes the final step in TAG biosynthesis along Kennedy pathway and is also the only rate-limiting enzyme of this pathway. To date, three DGAT families have been discovered, which are DGAT1, DGAT2 and DGAT3.

A Chinese Paper was published which was titled "the transcriptome sequencing and function annotation of lipid metabolism-related genes in the green microalga *Myrmecia incisa*" in the Journal of Shanghai Ocean University, volume 21, NO. 5, September 2012. In order to give a deep insight of the metabolic process of arachidonic acid and lipid in *Myrmecia incisa*, high through-put transcriptome pyrosequencing of *Myrmecia incisa* was conducted using the sequencer Roche 454 GS FLX, and a total of 382 468 high quality reads were obtained, which accounts for 97.14% of the original reads, with an average length of 322 nucleotides totally 123 Mb. After clustering and assembly using the CAP3 software, these reads were assembled into 22 714 contigs and 25 621 singletons. Homology search, comparison and annotation and classification of gene function were performed against public data bases, and the lipid metabolism pathway in *Myrmecia incisa* Reisigl was established based on the annotated genes in the transcriptome. But this paper does not disclose *Myrmecia incisa* Reisigl diacylglycerol acyltransferase cDNA sequence, and it is recognized by those skilled in the art that the method of high-throughput sequencing is not 100% accurate and is highly possible for inaccuracy, thus according to the paper, a person of ordinary skill in the art is difficult to obtain the accurate gene sequence of *Myrmecia incisa* Reisigl diacylglycerol acyltransferase.

Chinese patent document CN201210477507.7 whose date of publication is Feb. 27, 2013, titled "a DNA sequence coding *Myrmecia incisa* Reisigl diacylglycerol acyltransferase and the use thereof shows that based on *Myrmecia incisa* Reisigl transcriptome sequencing data, a full-length cDNA sequence of a *Myrmecia incisa* Reisigl diacylglycerol acyltransferase (MiDGAT2) gene was obtained by screening. Homology alignment analysis indicated that the *Myrmecia incisa* Reisigl diacylglycerol acyltransferase gene was of the DAGT2-gene family. Further obtained was the full-length DNA sequence of MiDGAT2. Heterologous expression in a TAG synthesis defective strain H1246 of yeast, proved that the protein encoded by the gene has the capability of triacylglycerol synthesis. However, *Myrmecia incisa* Reisigl is a eukaryotic alga, and it may contain more than one diacylglycerol acyltransferase, and TAG synthesis may be catalyzed by multiple isozymes. An isozyme/isoenzyme refers to an enzyme that has different properties (different Vmax and/or Km) but catalyzes the same reaction, which is also called isofunctional enzymes. The amount of isoenzymes may vary between different organs and tissues in an organism, and the isoenzymes may also appear in different organelles of any eukaryotic cells. Their differences can be shown in the primary and quaternary structure of protein, or in the process after translation. Their enzymatic activity can be regulated in response to specific physiological conditions in the cell. Isoenzyme is the result of gene variation; while gene variation is the molecular evolution during the evolution process in order to adapt to the increasingly complex metabolism. Gene differentiation facilities the adaptation of different metabolic needs in different tissues or different organelles, and is the protein phenotype of gene coding. Therefore, finding and investigating *Myrmecia incisa* Reisigl diacylglycerol acyltransferase gene sequence is of great importance to the study of *Myrmecia incisa* Reisigl evolution, genetic variation and provides a new method of synthesizing TAG by genetic engineering.

SUMMARY OF THE INVENTION

The purpose of this invention is to provide an isolated polypeptide against the drawbacks in prior art.

The second purpose of this invention is to provide an isolated polynucleotide.

The third purpose of this invention is to provide a recombinant expression vector.

The fourth purpose of this invention is to provide a genetically engineered host cell.

The fifth purpose of this invention is to provide a use of the above polypeptide, polynucleotide, recombinant expression vector and host cell.

To achieve the first purpose above, this invention takes the following technical solutions: an isolated polypeptide, the amino acid sequence of the isolated polypeptide is shown as SEQ ID NO. 3.

To achieve the second purpose above, this invention takes the following technical solutions: an isolated polynucleotide comprising a nucleotide sequence selected from the group consisting of:
a) a polynucleotide encoding the polypeptide as described above; or
b) a polynucleotide complementary to the nucleotide sequence in a).

In a preferred embodiment the nucleotide sequence is selected from the group consisting of:
a) a nucleotide sequence shown in SEQ ID NO.1 or SEQ ID NO 0.2; or
b) a nucleotide sequence that is complementary to the nucleotide sequence in a).

To achieve the third purpose above, this invention takes the following technical solutions: a recombinant expression vector, the recombinant expression vector is constructed with a plasmid or virus and a polynucleotide as described above.

In a preferred embodiment the plasmid is pYES2.

To achieve the fourth purpose above, this invention takes the following technical solutions: a genetically engineered host cell, the genetically engineered host cell is selected from one of the following:
a) a host cell and progeny thereof transformed or transduced with the polynucleotide as described above;
b) a host cell and progeny thereof transformed or transduced with the recombinant expression vector as described above.

In a preferred embodiment, wherein the host cell is a bacterial cell, a fungal cell, a plant cell, an animal cell or any progeny of these host cells.

In a preferred embodiment, the host cell is a yeast cell.

To achieve the fifth purpose above, this invention takes the following technical solutions: Use of the polypeptide, the polynucleotide, the recombinant expression vector, the any host cell in the production of triacylglycerols.

In a preferred embodiment, the use is catalyzing the conversion of C18:1 fatty acid into triacylglycerol.

The advantages of this invention are:

In the present invention a 309-bp gene fragment highly similar to the known DGAT gene is obtained based on the *Myrmecia incisa* transcriptome sequencing data. On the basis of the sequence of the fragment, the full-length cDNA sequence of the gene is cloned using the Rapid Amplification of cDNA ends (RACE). Through homology comparison analysis, it is confirmed that the *Myrmecia incisa* Reisigl diacylglycerol acyltransferase gene belongs to DAGT2 gene family, and the full-length gene sequence is further obtained by cloning. Through expression of the gene in a yeast TAG synthesis-defective strain H1246, i.e. gene functional complementation experiment, it is shown that the coded protein has the capability of TAG synthesis, which proves the function of the gene; and a substrate preference experiment proves that the coded protein of the gene has C18:1 fatty acid preference. The cloning of the gene provides a novel approach for large-scale TAG synthesis through genetic operation.

DETAILED DESCRIPTION OF THE PREFERRED EMBODIMENTS

Figure 1:
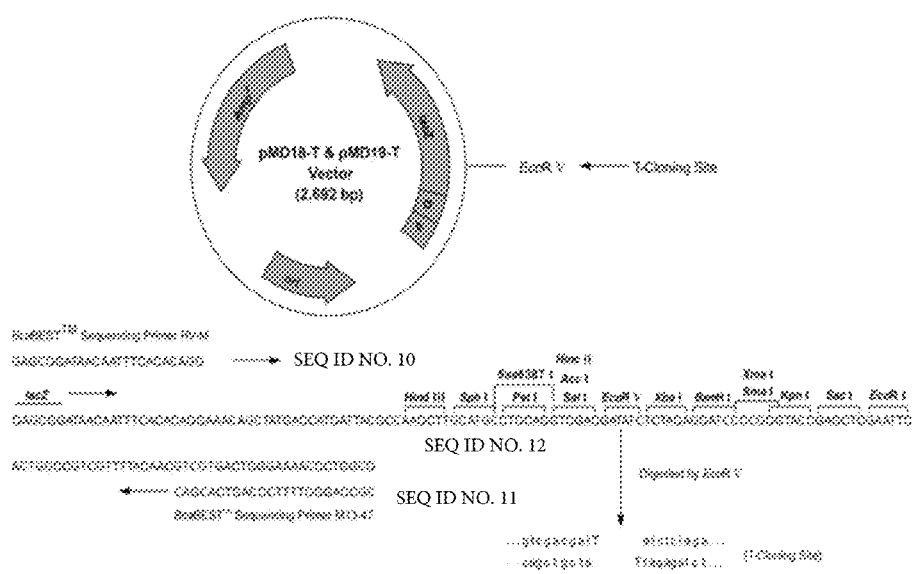
FIG. 1: map of the vector pMD19T.

Technology pathway of the present invention is:
1) *Myrmecia incisa* was cultured in BG-11 medium at the temperature of 25° C. and light intensity of 115 μmol photons $m^{-2} \cdot s^{-1}$. Algal cells were collected for genomic DNA and RNA extraction.
2) A 309 bp sequence highly similar to the known DGAT gene was obtained from *Myrmecia incisa* Reisigl transcriptome sequencing data through screening. Based on the sequence of the fragment, the full-length cDNA sequence of *Myrmecia incisa* Reisigl diacylglycerol acyltransferase gene is cloned using the method of RACE, and sequence alignment shows that it is different from another cDNA sequence cloned by our research group in China patent application (Application No: CN201210477507.7) in that the two sequences only share a 48% homology. For this reason, we designated the *Myrmecia incisa* Reisigl diacylglycerol acyltransferase gene obtained in the present invention as MiDGAT2B. Then cDNA from reverse-transcribed RNA of *Myrmecia incisa* was used as templates for MiDGAT2B full-length cDNA sequence validation.
3) PCR primers were designed according to full-length cDNA sequence of MiDGAT2B, and *Myrmecia incisa* Reisigl genomic DNA was used as template for PCR amplification to obtain full-length DNA sequence of MiDGAT2B.
4) PCR primers were designed according to full-length cDNA sequence of MiDGAT2B; pMD19T/MiDGAT2B plasmid was constructed using PCR.
5) pYES2 Vector and pMD19T/MiDGAT2B plasmid were double-digested using restriction endonucleases XbaI and EcoRI, target fragments were extracted and ligated using T4 DNA ligase, forming the recombinant expression vector pY-MiDGAT2B.
6) The recombinant expression vector pY-MiDGAT2B was transformed into yeast defective strain H1246 by electroporation; transgenic yeast Y-MiDGAT2B was screened by culturing in a uracil synthesis-defective culture medium (SC-U medium).
7) Transgenic yeast H1246 strain, yeast H1246 strain transformed with empty vector, non-transgenic yeast H1246 strain and wild type yeast Scy62 were inoculated into SC-U medium, and yeast cells were harvested and freeze-dried after 72 hours.
8) The total lipid contents of the yeast cells were analyzed by thin layer chromatography (TLC); the result confirmed that the transgenic yeast Y-MiDGAT2B contains TAG Meanwhile, transgenic, defective and wild type yeast cells were stained with oil body-specific fluorescent dye Bodily, and it was found that lipid droplets were reestablished in the transgenic yeast Y-MiDGAT2B, proving that—the MiDGAT2B coded protein is capable of TAG synthesis.

9) Determination and analysis of the substrate preference of MiDGAT2B zymoprotein encoded by MiDGAT2B.

The terms "Polypeptide of the invention", "MiDGAT2 coded protein", "MiDGAT2B zymoprotein" or "MiDGAT2B protein" as used interchangeably herein, refer to a protein or polypeptide that has the amino acid sequence of DGTA shown in SEQ ID NO.3. Such polypeptides may be synthesized with or without an initial methionine, and with or without the signal peptide.

The terms "gene of the invention" and "MiDGAT2B", as used herein, refer to polynucleotide that encode polypeptides with diacylglycerol acyltransferase activity (SEQ ID NO. 1 or SEQ ID NO.2). The gene sequence may or may not include coding sequence of signal peptide.

The term "isolated", as used herein, refers to material removed from its original environment (for natural substances, original environment means natural environment). For example, a polynucleotide or a polypeptide naturally present in the cells of a living organism is not "isolated," but the same polynucleotide or polypeptide, if separated from the coexisting materials of its natural state, is "isolated".

The terms "isolated MiDGAT2B protein or polypeptide", as used herein, refers to MiDGAT2B polypeptide substantially free of other naturally related proteins, lipids, carbohydrates, or other materials. One skilled in the art can purify MiDGAT2B protein using standard techniques for protein purification. The substantially pure polypeptide will yield a single major band on a non-reducing polyacrylamide gel. The purity of MiDGAT2B polypeptide can be analyzed by the sequence analysis of the amino acids.

The polypeptides of the present invention may be recombinant polypeptides, natural purified polypeptides, or synthetic polypeptides. Preferably, it is a recombinant polypeptide.

Polypeptides of the present invention include naturally purified products, or products of chemical synthetic procedures, or products produced by recombinant techniques from a prokaryotic or eukaryotic host, including, for example, bacterium, yeast, higher plant, insect and mammalian cells. Depending upon the host employed in a recombinant production procedure, the polypeptides of the present invention may be glycosylated or non-glycosylated. Polypeptides of the invention also may or may not include an initial methionine residue, and may or may not include signal peptide.

Polynucleotides of the invention may be in the form of DNA or RNA. The form of DNA includes cDNA, genomic DNA, or synthetic DNA. The DNA may be double-stranded or single-stranded. The DNA can be coding strand or non-coding strand. The coding sequence which encodes the mature polypeptide may be identical to the coding sequence shown in SEQ ID NO.2 or is a degenerate variant of this sequence.

The polypeptides and polynucleotides of the present invention are preferably provided in an isolated form. More preferably, it is purified to homogeneity.

The full-length nucleotide sequence of MiDGAT2 of the present invention and their fragments can be obtained using PCR amplification, DNA recombinant techniques, or artificial synthesis. As to PCR amplification, PCR primers can be designed according to the nucleotide sequence disclosed in the invention, especially to the open reading frame, and commercial cDNA library or any cDNA library prepared according to routine method known in the art is used as template for the amplification of the relevant sequence. When the sequence is long, two or more rounds of PCR amplification are normally required and the amplified fragments are then assembled in correct order.

Once the relevant sequence has been obtained, it can be obtained in large quantities by recombination technology, which involves cloning the sequence into vectors, transforming the vectors into cells and then isolating the relevant sequence from the propagated host cells by conventional methods known in the art. Furthermore, the relevant sequence can also be obtained by artificial synthesis, especially when the fragment is short in length. Usually, multiple small fragments are synthesized before they are ligated to form a long fragment.

Currently, DNA sequence coding for the protein (or the fragment and derivative therein) of the present invention may well be produced by conventional methods of chemical synthesis or by DNA recombination techniques. The DNA sequence may then be incorporated into various DNA molecules (say a vector) and host cells known in the art. In addition, synthetic chemistry may be used to introduce mutations into the protein sequence of this invention.

PCR amplification of genomic DNA/RNA is particularly preferred for obtaining the gene in the present invention. When full length cDNA is difficult to obtain from a library, RACE (Rapid Amplification of cDNA ends) may be preferably used. PCR primers can be appropriately selected according to the disclosed sequence information within the present invention, and can be synthesized by routine, conventional methods. Conventional methods, like native polyacrylamide gel electrophoresis, may be used to isolate and purify amplified DNA or RNA.

The present invention also relates to a vector comprising the polynucleotide in the invention and a host cell generated by genetic engineering with the vector or MiDGAT2B protein-coding sequences.

Recombinant MiDGAT2B peptides can be expressed or produced with the polynucleotide sequence of the present invention by recombinant DNA technology; generally the following steps are included:

(1) Transformation (including transfection, transduction, or infection) of a polynucleotide encoding MiDGAT2B polypeptide or an expression vector comprising the polynucleotide of the present invention into a suitable host cell;
(2) Culturing the host cell in a suitable medium;
(3) Isolation and purification of the protein from the medium or the host cell.

In the present invention, MiDGAT2B polynucleotide sequence can be inserted into a suitable recombinant expression vector and expressed in a suitable host. The term "recombinant expression vector" refers to a yeast or bacterial plasmids, bacteriophages, yeast plasmids, plant cell viruses, mammalian cell viruses such as adenoviruses, retroviruses or other carriers. Any other plasmid or vector may be used as long as they are replicable and viable in the host. The vector is typically a plasmid provided with an origin of replication, a promoter for the expression of the polynucleotide, a marker gene and translational control elements.

The embodiment of the invention is further described with figures, but the protection scope of this invention is not restricted to the scope of disclosure in the following experiments. The experimental methods, whose specific conditions are not given in the following examples, are generally conventional conditions, such as those described, for example, in Molecular Cloning, A Laboratory Manual, Sambrook and Russell (2001) Cold Spring Harbor Press, or recommended by manufacturers. Unless otherwise described, the percentage and the copies are calculated by weight.

Example 1

1. Materials

Figure 2:
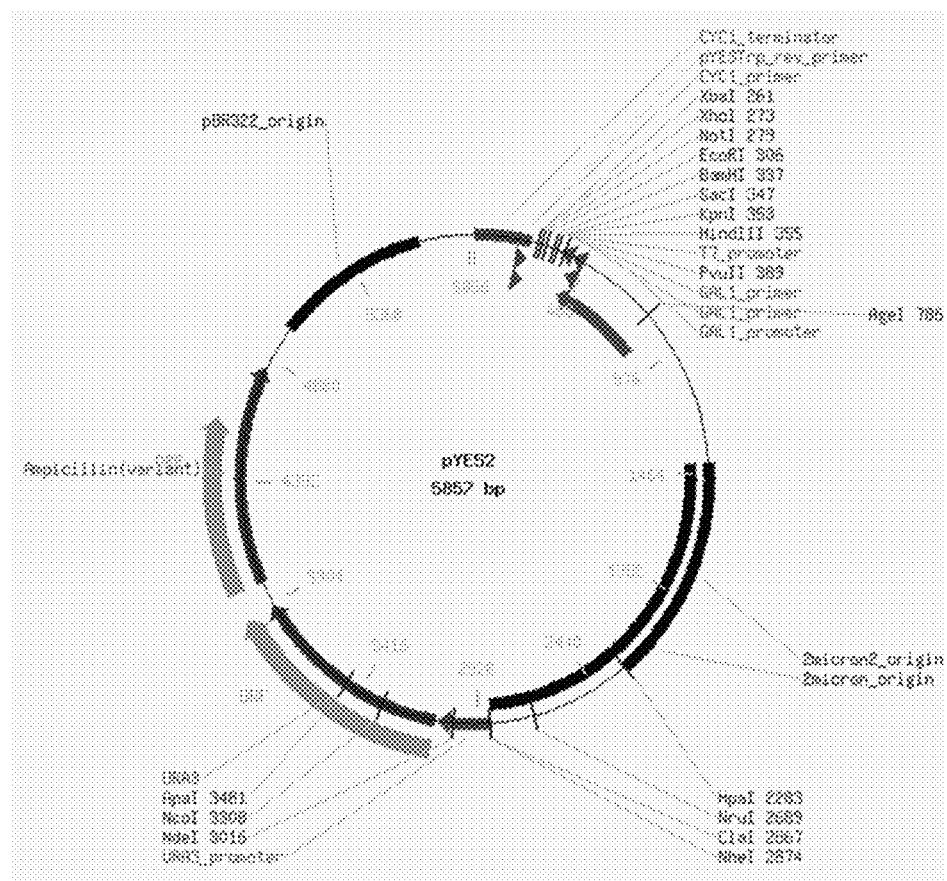
FIG. 2: map of the vector pYES2.

1) The freshwater microalga *Myrmecia incisa* H4301 was commercially provided by CAUP (Culture collection of algae of Charles University of Prague). The alga was cultured at 25° C., at a light intensity of 115 µmol photons m$^{-2}$·s$^{-1}$ with a light-dark period 12 h/12 h in BG-11 medium.
2) Vector of pMD19T (vector map shown in FIG. 1) and pYES2 (vector map shown in FIG. 2) were purchased from Invitrogen Corp. Yeast mutant strains H1246 and Scy62 were provided by Dr. Stymne's Laboratory in the Swedish University of Agricultural Sciences. The strains were inoculated in SC medium at 30° C. and shaken at 200 rpm. SC medium was obtained from Shanghai MeiLian Bio Technology Co. Ltd. SMART™ RACE cDNA amplification kit was purchased from Clontech. Fluorescent dye specific for the oil body in live yeast Bodipy was purchased from GENMED SCIENTIFICS INC. U.S.A. TAG standard was purchased from Nu-Chek Company, UK.

2. Methods 1) 100 mg of fresh *Myrmecia incisa* Reisigl cells was placed in pre-cooled mortar and liquid nitrogen was added before the *Myrmecia incisa* Reisigl cells were fully ground.
2) DNA was extracted by the CTAB method, total cellular RNA was isolated using the Trizol method, and the samples were stored at −20° C. until use.
3) Based on the *Myrmecia incisa* Reisigl transcriptome sequencing data, a 309 bp gene fragment was screened out, which shares high similarity to known DGAT gene sequences. Primers were designed according to the fragment, and PCR reactions were run using the SMART™ RACE cDNA amplification kit. The 5'-RACE was performed using nested PCR, wherein the first-round PCR reaction was carried out using the following conditions: denaturation at 94° C. for 30 s, annealing at 68° C. for 30 s, and extension at 72° C. for 2 min, with a total of 30 cycles; the amplification primers are GSP1 (AGGTCGCCTGTGAACTTGGGGATGT, SEQ ID NO.4) and UPM. 1.5 µL of the products of this first-round PCR then used as the template in the second-round PCR, wherein the conditions are as follows: denaturation at 94° C. for 30 s, annealing at 70° C. for 1 min, and extension at 72° C. for 2 min with a total of 30 cycles; the amplification primers were GSP2 (ACGGTGACATGGCGCACAGGGTTGG, SEQ ID NO.5) and NUPM. The condition of the 3'-RACE PCR is identical to that of the second-round PCR of 5'-RACE. Subsequently, the PCR product was recovered in gel, TA-cloned and then submitted to Shanghai Sangon Biological Engineering Co., LTD for sequencing. The sequenced 5'- and 3'-fragments were assembled with the known fragment, and the full-length cDNA nucleotide sequence of MiDGAT2B was obtained.
4) PCR primers were designed according to the MiDGAT2B full-length cDNA sequences obtained by RACE: MiDGAT2BF:5' CAGTTACAAATCGCGTTCTGCTTA 3'(SEQ ID NO.6); MiDGAT2BR:5' TCCCCAGTCAAGAGTGTGCTACTC 3'(SEQ ID NO.7), the cDNA generated through reverse transcription of the *Myrmecia incisa* Reisigl total RNA was used as template for PCR amplification. The PCR reaction condition is as follows: pre-denaturation at 94° C. for 5 min; 35 cycles of denaturation at 94° C. for 30, annealing at 64° C. for 45 s, and extension at 72° C. for 2 min; followed by extension at 72° C. for 10 min. The PCR products were gel-purified, inserted into pMD19T-vectors, and then transformed into *Escherichia coli* DH5α competent cells. After blue-white selection the positive clones were picked and validated by colony PCR, and was submitted to Shanghai Sangon Biological Engineering Co., LTD for sequencing to confirm the DNA sequence of *Myrmecia incisa* Reisigl MiDGAT2B.
5) PCR primers were designed according to the full-length cDNA sequence of MiDGAT2B, and *Myrmecia incisa* Reisigl genomic DNA was used as template for PCR amplification. PCR reaction condition is as follows: pre-denaturation at 94° C. for 5 min; 35 cycles of denaturation at 94° C. for 45 s, annealing at 64° C. for 45 s, and extension at 72° C. for 2 min; followed by extension at 72° C. for 10 min. The full length DNA sequence of *Myrmecia incisa* Reisigl MiDGAT2B was obtained by recovering the PCR product as described above, TA-cloning and sequencing by Shanghai Sangon Biological Engineering Co., LTD.
6) PCR primers were designed according to MiDGAT2B full-length cDNA sequences: the upstream primer F: gaattcAAAATGGAGCTGGCCTCAGC (SEQ ID NO.8, lower case letters represent restriction site for EcoRI, and the sequence AAA is the consensus sequence of yeast); downstream primer R: tctagaCTACTCGATGATGTGCAG (SEQ ID NO.9, lower case letter represent restriction site for XbaI), both of which harbor the restriction sites for XbaI and EcoRI. The plasmid of pMD19T/MiDGAT2B was constructed by PCR method. Each 25 µL PCR reaction mixture contained 2.5 µL of Ex Taq buffer, 2 µL of dNTP, 2 µL of Mg$^{2+}$, 2 µL of cDNA template, 1 µL of each primer, 0.25 µL of Ex Taq polymerase and 14.5 µL of sterile water. The amplification condition is as follows: pre-denaturation at 94° C. for 5 min; 35 cycles of denaturation at 94° C. for 45 s, annealing at 64° C. for 45 s, and extension at 72° C. for 2 min; followed by extension at 72° C. for 10 min. The PCR product was recovered, TA cloned and submitted to Shanghai Sangon Biological Engineering Co., LTD for sequencing to confirm the accuracy of sequence, as described above.
7) Plasmid pMD19T/MiDGAT2B was extracted from the *Escherichia coli* DH5α and double digested using the restriction endonucleases XbaI and EcoRI. Meanwhile, the plasmid pYES2 was also double digested using the restriction endonucleases XbaI and EcoRI. The reaction mixture contained 4 µL of 10×M buffer solution, 4 µL of 0.1% BSA, about 2 micrograms of DNA, 1 µL each of XbaI/EcoRI, and RNase-free water was added to reach a final volume of 20 µL. The plasmids were digested at 37° C. for 4 hours, and the target MiDGAT2B gene fragment was gel-recovered and ligated to the pYES2 fragment using T4 DNA ligase, resulting in the recombinant expression vector pY-MiDGAT2B. The reaction condition for the ligation is: 2.5 µL of buffer solution, about 0.3 pmol of DNA (MiDGAT2B), 0.03 pmol of DNA vector (pYES2 fragment), 1 µL of T4 DNA Ligase, and RNase-free water was added to reach a final volume of 25 µL. The ligation was carried out at 16° C. overnight. The plasmid was subsequently transformed into *Escherichia coli* DH5α competent cells, and cloning, PCR validation and sequencing were preformed as described above. The plasmid pY-MiDGAT2B was extracted from *Escherichia coli* DH5α and stored at −20° C. until use.
8) Preparation of yeast competent cells. The yeast was inoculated in SC medium, recovered and incubated at 30° C. overnight, then the culture was scaled up in the proportion of 1:100 with shaking at 200 rpm until the cell density reached the concentration of $10^8$ cells/mL (about 4-5 hours). The cells were chilled on ice for 15 min to stop the cell growth, and collected by centrifugation at 5000 rpm for 5 min at 4° C. and washed three times in pre-cooled sterile water and then collected by centrifugation under the aforementioned conditions. Then the cells were washed once with 1M pre-cooled sorbitol and dissolved in 0.5 M pre-cooled sorbitol to reach a final cell concentration of $1\times10^{10}$ cells/mL. The cells were stored on ice for electroporation.

9) The recombinant expression vector pY-MiDGAT2B was transformed into yeast H1246 competent cell by electroporation using electroporator (Bio-Rad). 5~10 µL (5~200 ng) recombinant expression vector to be transformed were pre-cooled on ice and mixed with the competent cells and incubated in a electroporation cuvette (0.2 cm electrode gap, Bio-Rad) on ice, then the mixture of DNA and cells was transferred to a pre-cooled electroporation cuvette and gently mixed. After ice bath for 5 min, the program Sc2 was selected and electric-shock was performed once. Then the electroporation cuvette was removed and 1 mL of pre-cooled sorbitol (1M) was added immediately, and the mixture was gently moved to new YPD medium, shaken for 5 h at 30° C. And the liquid containing yeasts was spread on SC-U medium containing 1M sorbitol, and kept at 30° C. for 48-72 h upside-down. Colonies were picked and grown in SC-U liquid medium. After colony PCR validation, strains were preserved in SC-U medium containing 2% glucose. In addition, empty pYES2 vector was transformed into yeast H1246 competent cells in the same way as described above.

10) The preserved liquid containing yeast was inoculated in SC medium, cultured at 30° C. for 72 hours with shaking at 200 rpm and collected and freeze-dried.

11) The total lipids of the freeze-dried yeast were extracted through the following method: accurately weigh 50 mg of yeast powder in the test tube, add 1 mL of chloroform/methanol (1:2) followed by addition of 200-300 µL of glass beads and vortex for 15 min. Complete disruption of the cell wall was checked by observation under microscope. Centrifuge the cells for 15 min at 4000 rpm, and then remove the supernatant to a fresh tube. Add 400 µL of 50 mM citric acid and 600 µL of chloroform, mix thoroughly, and centrifuge for 15 min at 4000 rpm. Withdraw the lower layer of the solution with care, place the solution in the esterifying bottle and dry through.

12) The triacylglycerol of transgenic yeast was examined by thin layer chromatography (TLC). Hexane-diethylether-glacial acetic acid (80/20/1, v/v/v) was used as developing agent. Chromogenic agent: a solution containing $CuSO_4 \cdot 5H_2O$ (10%, w/v) and phosphoric acid (8%, v/v). 30 µL of chloroform was added into the total lipids extracted from yeast, the sample was loaded onto silica gel 60 F254 plate (Merck) with capillary tube. The plate was developed in a chromatography cylinder, taken out and sprayed with chromogenic agent before it was held at 140° C. for 10 min.

13) The live yeast was stained with the oil body-specific fluorescent dye Bodipy, observed under laser confocal microscope (Leica) and photos were taken.

14) Substrate preference experiment of MiDGAT2B protein: Hexane-diethyl ether-glacial acetic acid (80/20/1, v/v/v) as developing agent. Chromogenic agent: a solution containing $CuSO_4 \cdot 5H_2O$ (10%, w/v) and phosphoric acid (8%, v/v). 30 µL of chloroform was added into the total lipids extracted from yeast, the samples were loaded onto silica gel 60 F254 plates (Merck) with capillary tube, the TLC plate was developed in a chromatography cylinder, taken out and dried in the air. The developed strip that contained TAG was collected under the ultraviolet wavelength (254 nm), ground into powder, which was eluted with hexane into the esterifying bottle, and dried with nitrogen ventilation for methyl esterification. 1 mL of 1M methanol solution containing 4% sulfuric acid was added. After being charged with nitrogen, esterification was carried out at 85° C. water bath for 1 h to thoroughly dissociate and methylate the binding fatty acid molecules. After the esterification, 1 mL of deionized water and 1 mL of hexane were added to esterifying bottle and mixed thoroughly, and the esterifying bottle was then centrifuged at 5500 rpm for 10 min. Supernatants were collected and concentrated using nitrogen, and stored at 4° C. The fatty acid components were analyzed by Agilent 6890 plus Gas Chromatography. The column is a HP-5 capillary column (30 m×0.25 mm). The temperature program was 50° C. for 1 min, increase by 25° C./min to a temperature of 200° C., and then increase by 3° C./min to 230° C. followed by a final incubation for 18 min. The split ratio was 50:1, the flow rate of nitrogen, hydrogen and air was 30 mL/min, 450 mL/min and 40 mL/min, respectively. The injection volume was 1 µL. The above experiment was carried out in triplicate.

3. Result

Figure 3:
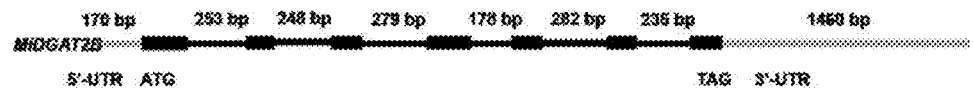
FIG. 3: Schematic representation of the structure of *Myrmecia incisa* Reisigl MiDGAT2B gene. The shaded box represents exons; the black line represents introns, the grey line represents untranslated region.

1) The cDNA full-length sequence of *Myrmecia incisa* Reisigl diacylglycerol acyltransferase gene (MiDGAT2B, SEQ ID NO.1) was obtained by RACE and validated by PCR amplification: its 5'-untranslated region (UTR) is 107 bp, its 3'-UTR 1460 bp and the open reading frame (ORF) is 1068 bp in length. PCR amplification reaction was performed using the *Myrmecia incisa* Reisigl genomic DNA as template. The products were submitted for sequencing and the full length sequence of MiDGAT2B (SEQ ID NO.2) was obtained. The DNA sequence of the gene is 4149 bp in length, possessing six introns with the length of introns I-VI being 253 bp (from 374 to 626 bp), 248 bp (from 754 to 1001 bp), 279 bp (from 1141 to 1419 bp), 178 bp (from 1613 to 1790 bp), 282 bp (from 1927 to 2208 bp), and 235 bp (from 2339 to 2573 bp), respectively, which divide the coding sequence into seven exons (FIG. 3). The amino acid sequence corresponding to the protein encoded by MiDGAT2B is shown in SEQ ID NO.3.

Figure 4:
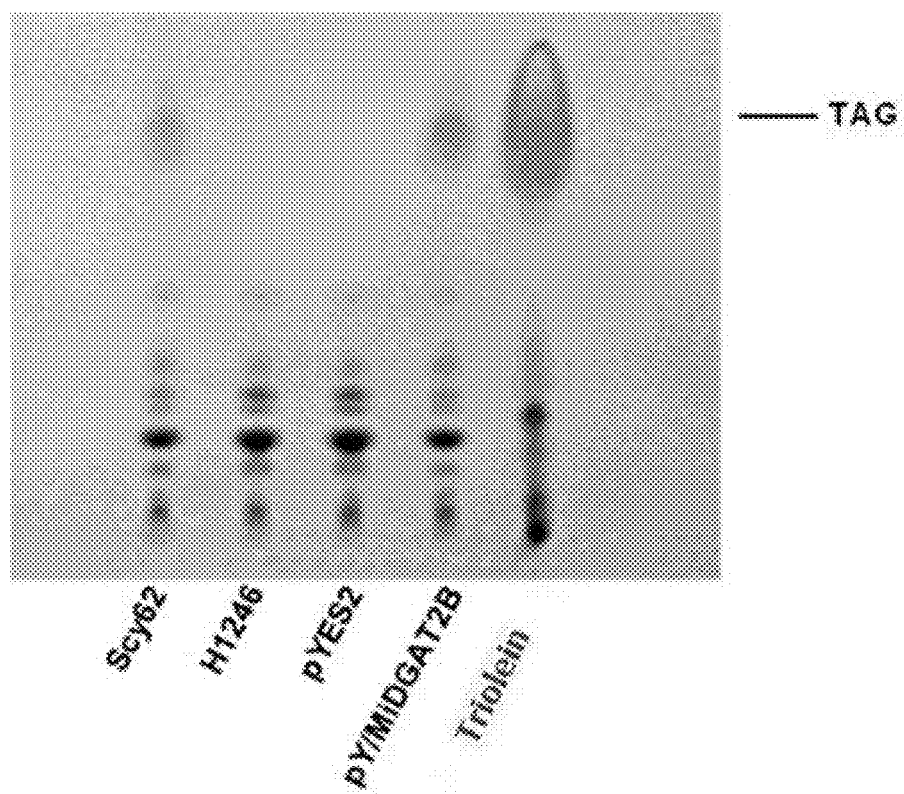
FIG. 4: thin-layer chromatograms of yeast lipids, wherein wild type yeast Scy26, defective strain H1246 defective strain with pYES2, defective strain transformed with MiDGAT2B and TAG standard are in order from left to right.

2) Transgenic yeast of Y-MiDGAT2B was cultured in SC medium with galactose as an inducer. The result of thin layer chromatogram (TLC) analysis of yeast lipids (FIG. 4) shows that the expression products of MiDGAT2B could restore the TAG-defective mutant H1246 to the ability to synthesize TAG.

Figure 5:
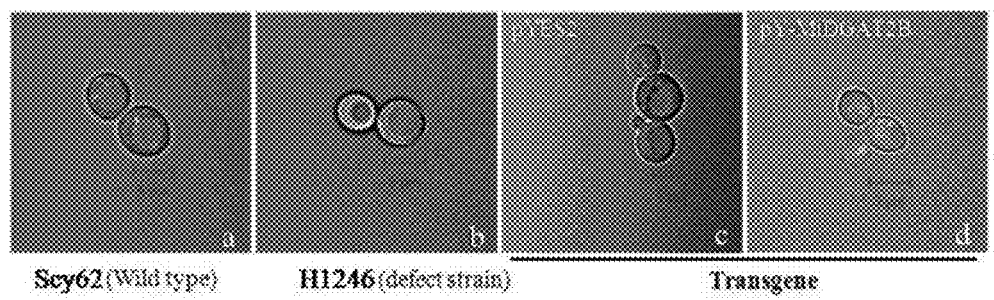
FIG. 5: Fluorescent staining of yeast cells with Bodipy, wherein wild type yeast Scy26, defective strain H1246, defective strain transformed with pYES2 and defective strain transformed with MiDGAT2B are in order from left to right.
Figure 6:
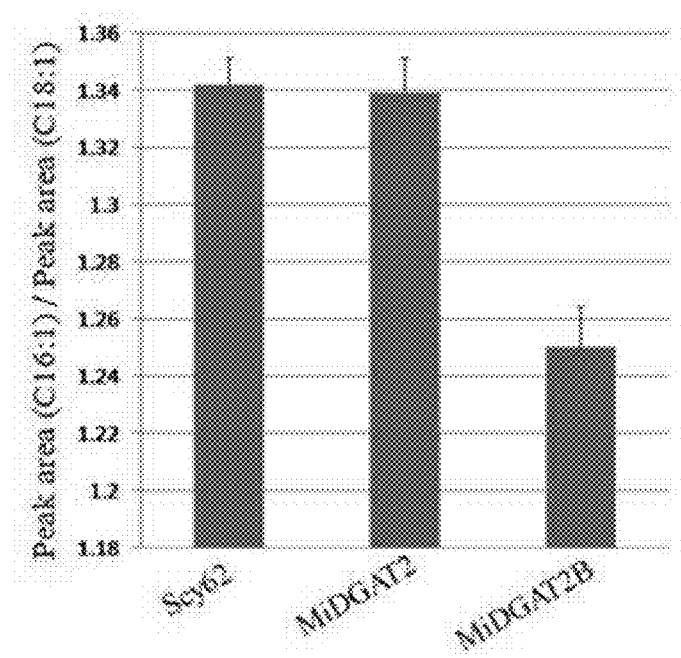
FIG. 6: Substrate preference analysis of MiDGAT2B zymoprotein.

3) The yeast cells were stained with oil body-specific fluorescent dye Bodipy. It was found that the oil body was reestablished in the transgenic yeast Y-MiDGAT2B compared with the TAG-defective mutant H1246 (FIG. 5), indicating that MiDGAT2B encodes a protein that is capable of synthesizing TAG 4) Yeast cells usually contain four kinds of fatty acids, i.e. C16:0, C16:1, C18:0 and C18:1. But its gas chromatography (GC) tests of TAG show that the yeast TAG mainly comprises C16:1 and C18:1 fatty acids. DGAT can functionally catalyze the transfer of an acyl group to the third carbon of the glycerol backbone of diacylglycerol to generate the triacylglycerol. Thus, the more C18:1 involved in TAG synthesis, the more C18:1 can be detected. To further analyze the substrate preference of MiDGAT2B protein and MiDGAT2 protein (The MiDGAT2 protein coded by the MiDGAT2 gene cloned in Chinese patent application CN201210477507.7), the peak area ratio of C16:1 to C18:1 was used as an indicator. The results (FIG. 6) show that the peak area ratio of C16:1 to C18:1 in the yeast strain transformed with MiDGAT2 is 1.3394, which is similar to that of the wild type Scy26 (1.3420). The experimental data was analyzed by SPSS 13.0 and the result showed that there is no significant difference ($P>0.05$). But the peak area ratio of C16:1 to C18:1 in the yeast strain transformed with MiDGAT2B is 1.2501, and there was a significant difference ($P<0.05$). These results show that there is significant difference between the substrate preference of MiDGAT2 and MiDGAT2B towards C16:1 and C18:1 with MiDGAT2B more in favor of using C18:1 as a substrate for the synthesis of TAG The present invention is not intended to limit to embodiments thereof. Further, it will be understood by those skilled in the art that various changes in form and details may be made therein without departing from the spirit and scope of the invention as defined by the appended claims.

The invention claimed is:

1. An isolated polynucleotide, wherein said isolated polynucleotide comprises the polynucleotide sequence shown in SEQ ID NO:1.

2. A recombinant expression vector, wherein said recombinant expression vector comprises the polynucleotide of claim 1.

3. The recombinant expression vector according to claim 2, wherein said plasmid is pYES2 plasmid.

4. A genetically engineered host cell and progeny thereof, wherein said host cell is transformed or transduced with the polynucleotide of claim 1.

5. The genetically engineered host cell and progeny thereof of claim 4, wherein the host cell is a bacterial, fungal, plant or animal cell.

6. The genetically engineered host cell and progeny thereof of claim 5, wherein the host cell is a yeast cell.

7. A genetically engineered host cell and progeny thereof, wherein said host cell is transformed or transduced with the recombinant expression vector of claim 2.

* * * * *

SEQUENCE LISTING

<160> NUMBER OF SEQ ID NOS: 12

<210> SEQ ID NO 1
<211> LENGTH: 2698
<212> TYPE: DNA
<213> ORGANISM: Myrmecia incisa

<400> SEQUENCE: 1

```
aagcagtggt atcaacgcag agtacgcggg ggcatcttcg aagcctgctt tggctttagt      60
gcaacgggta gggtcgcaac atagtcggtt tcaaaccagc gtgtatcaac tctctgttca     120
gctgttcaat ctgtcacagt tacaaatcgc gttctgctta gcaccgtgtg atggagctgg     180
cctcagcgaa gagctcgttt ctgtcagcgt ggcaacttgc ctgggccaag ctatcgtggg     240
cgaccagtct gatcctaccc aaagctgcgg ccatctacac tgttggcatc tacttcagca     300
cgccccagtg ctggctgttc acgctctacc tgctgttctg tgaggacgtg ctgattcgcc     360
tcctcgtggc cgggtacctg gcgtggatct ttgtggggcc tgggcgcgat gcagccaaga     420
atgtgacgtg gcgcccgtac atgcggcgct gggcttgtg gaactacctc gcggcctact     480
tccgcgcaga gcttgtcaag acagcagagc tggacccctc caagagctac ctgttcggcg     540
tgcaccccca tggcgtgctc accatggcgt cctggatcaa cttttcgacc gagagcactg     600
gcttcagcga caagttccca ggcatcgaga tgcacgtcgg cacgctcaac tggaacttcg     660
tcacgcccat cgcgcgcgag tttctgctga tgcatggcgc ctgcgatgtg acgcgcgaca     720
cgctgtgcgc gctgctgagc aggccgggc gcgctgtgat ggtggccatc ggtggtgcag     780
ctgaagcact gcatgcgttt ccgggcacct atgacctggt gttggccaag aggaagggct     840
ttgtgaaagt ggcgatgatg acaggcgcat cgctcgtccc cgtgctgtgc tttggtgaga     900
acgaggtgat gacgaccgtg aaagtggagc acggctcctt cacgcacaag ctgcagcgct     960
tcctcaaggg catcgtgggc ttcacgattc ccgtctgcta tggccgcggc ctgtttggca    1020
tccgctatgg catcctgccc aaccctgtgc gccatgtcac cgtcgtcggg gcgcccatcg    1080
acatccccaa gttcacaggc gacctgcaca gcgaggaagg gcaggcagcc gtcaaccgag    1140
cgcacgcaaa gtacatcgcc gcgctgcagg ctttgtggga gcagcacaag gaccagtatg    1200
ccaagcagag gcgcagcagc ctgcacatca tcgagtagca cactcttgac tggggaaccc    1260
tgtccgtgta ggtctcggca cgatcccaga catgcctggg gtgaagcagc atgtctgaat    1320
acccttgacg ttttcacagc cttgatgttt ccgcagcctg cacctcatcg agtcgcgagt    1380
gcaagcccga taccctgcgg cctcggcccg ttttccagcc agccagggtg tagcagcccg    1440
cacatcgtag agtagcagca tggtgggttt ggctcgggcg aagcaccctcg ccagcgggaa    1500 cttcttgagg cttaatctat gcagggtgc agaggaatgc cacattgaat gtcatcacat    1560
aagattgctt atgaaaggca gctttcgtga accgctttca gcgcaatggt gcaggaccac    1620
gtgagggcat gtgactatga gtggcacact ttgccaagct gcagggggtc agcctgctga    1680
tcaggaacgg cttttgtggtt tcggacctct ggaggactat gttggtcatc ctcggggctt    1740
```

```
gacacgctta cctggtggtc tttgtaggtt gtgcaagttt agtttcaagt tggcaccggc    1800
agtggccccc cgtgtatgtg ggctgcacag ctgagaagcc tggttttgta catgctggtg    1860
cggcaggtat gggcaacatg tcagagtggc aagcacaagt catgcagggt agaccatcag    1920
ggtgatatct gcatcgactt cgtgcggtct ggactgactg aggcttggct ttgtgaggct    1980
tgccttgcct tttgtgtcat gttccagaag aacacagctg ctgcaaacct tgtggatgtt    2040
ggtcatgtga tgcctgcacc tcgcaggcgt ctcagctgac acattatggc tattgcggtg    2100
actatgcgtc tcccgtcttt gagcgcagaa cagggttcca gtggatcagg aagtatttgg    2160
tcggatggtg tggttgagct caagaacgag tggtttggtc aggtctagat ctcagctcgg    2220
gtgagtgctt ttccagaagt agcttggttg ctggctgggt gttcaccata gggtttgtat    2280
gtttgtcggc gtccgttgtt ccatgatcat attgaagggc tgggttgtaa tcagatgatc    2340
atgttagtgt ttttgtccgg gttgacttgt ggttcgtcac gctagcgtgg tgcctagtgg    2400
ttagggtgta gcgcagcatc gctgccgaat aatggacatg atgtcaagcg cctattcagg    2460
aggtgcttgc tacatgctgt cgaccacatc agtgcgcatg ggtcctgcgc tattggctgt    2520
gtgcttaggc taggtagggt tgtgtaggtg ttgaccatca gtggacagcc tctgcagtgt    2580
gtgttatgca gagctgctcg tgcccgatca caggcatagt gtgaggcttg ggatggcagt    2640
gccagttaca cgacgttgta aaatgatttg gctcaaaaaa aaaaaaaaa aaaaaaaa     2698

<210> SEQ ID NO 2
<211> LENGTH: 4149
<212> TYPE: DNA
<213> ORGANISM: Myrmecia incisa

<400> SEQUENCE: 2
aagcagtggt atcaacgcag agtacgcggg ggcatcttcg aagcctgctt tggctttagt      60
gcaacgggta gggtcgcaac atagtcggtt tcaaaccagc gtgtatcaac tctctgttca     120
gctgttcaat ctgtcacagt tacaaatcgc gttctgctta gcaccgtgtg atggagctgg     180
cctcagcgaa gagctcgttt ctgtcagcgt ggcaacttgc ctgggccaag ctatcgtggg     240
cgaccagtct gatcctaccc aaagctgcgg ccatctacac tgttggcatc tacttcagca     300
cgccccagtg ctggctgttc acgctctacc tgctgttctg tgaggacgtg ctgattcgcc     360
tcctcgtggc cgggtaagtt tcccagttga ccctgatgat tcttgcttga agctgggcct     420
gtccttgtta acaaagctgt gctgccgtgc ttgaggctgt aggaaactgt ggcgaatatt     480
caagaagtcg ttgacagaac ttcctgctgg cagttgggca cgttccgctg gtgcaccgtg     540
gcacgtctat gcatttcagt cttgagtgca aagcagtacg gtggcacgga ccgaacgctg     600
acctcacctc gcgctgtctg tggcaggtac ctggcgtgga tctttgtggg gcctgggcgc     660
gatgcagcca agaatgtgac gtggcgcccg tacatgcggc gctggggctt gtggaactac     720
ctcgcggcct acttccgcgc agagcttgtc aaggtgactg ccatcatat caatgccagg     780 acctccaaag cagatgggta ttgctgctgc cttggtgctg catcagggtt ctgaggcccg     840
cttgagggca acaacatttg tgtgttccgc cggctctgtc tagggcacgc cacaaaacaa     900
cccacaagag aagaggtctc tgtataccat ctagcagcct tccgcaccta ttcgcacacc     960
```

-continued

```
gtagccgctg ccttgacatg ttttcgtcgt gcaccatgca gacagcagag ctggacccct    1020
ccaagagcta cctgttcggc gtgcaccccc atggcgtgct caccatggcg tcctggatca    1080
acttttcgac cgagagcact ggcttcagcg acaagttccc aggcatcgag atgcacgtcg    1140
gtgagctgcg ctggatccgg cacatgctgc attccgacac cttttgtgct tggcaacagt    1200
cacgatgtgc tcgcacagtg ctagtctgct ggcaggtaca tggttctggc gtgatgtcat    1260
gatactgtgt gctgcttctc cttccagcaa cggcaatgtg cctttgccag tcatacggtt    1320
gtgctgacct tacaggttga acaatgttca gttggggta tgttacaccc attgcgctca     1380
tcgccccctt catgccatgc acgctgtgct gcctggcagg cacgctcaac tggaacttcg    1440
tcacgcccat cgcgcgcgag tttctgctga tgcatggcgc ctgcgatgtg acgcgcgaca    1500
cgctgtgcgc gctgctgagc aggccggggc gcgctgtgat ggtggccatc ggtggtgcag    1560
ctgaagcact gcatgcgttt ccgggcacct atgacctggt gttggccaag aggtaagcaa    1620
tcgaccattg ttgaagtagt gatcagggca gcgaccagtc tgctgcatgc agtgagtgta    1680
tgatacctga caggttgctt gctgtgcctg tgctgtgctt ctgtgccatc cttgctgttc    1740
tgcgtcaagt gctggatgcg ttgatcgatc tgctgcgtgc tgcgctgcag gaagggcttt    1800
gtgaaagtgg cgatgatgac aggcgcatcg ctcgtccccg tgctgtgctt tggtgagaac    1860
gaggtgatga cgaccgtgaa agtggagcac ggctccttca cgcacaagct gcagcgcttc    1920
ctcaaggtag gatcacagag gaccaagtca atattgggta tttggtagat gtcatgtgtc    1980
gtcgtggcat caactgttgc aaggtcagcg ttcaatacag ttgtggctgc tcggattcag    2040
caagggtgtc tgcaagggct cgtagctcgc cgctgatata acatgtttgt cagattatgc    2100
caggcctgaa cactgcgcca gagctaacac gctgcacgca accccatggc atccaggccc    2160
atgccagctc agcacgacat gtcttgacac ctggcatgcc taatgcaggg catcgtgggc    2220
ttcacgattc ccgtctgcta tggccgcggc ctgtttggca tccgctatgg catcctgccc    2280
aaccctgtgc gccatgtcac cgtcgtcggg gcgcccatcg acatcccaa gttcacaggt     2340 gagcccaagc aagcccagc tagcatcctt ctgcttggaa tgttcagcat aaactcgtga     2400
agtgtgtgct tggttagcat gcatgctcaa gcagctttct tccgaatgag agtgacccgc    2460
acacgcggga agtgcagtag gcggtcgtcg ccacggtgcg tgccaatcat ggccttgtgg    2520
cccgagctgt ttggcacatg tattgttgag agagagctct caatgccgtg caggcgacct    2580
gcacagcgag gaagggcagg cagccgtcaa ccgagcgcac gcaaagtaca tcgccgcgct    2640
gcaggctttg tgggagcagc acaaggacca gtatgccaag cagaggcgca gcagcctgca    2700
catcatcgag tagcacactc ttgactgggg aaccctgtcc gtgtaggtct cggcacgatc    2760
ccagacatgc ctggggtgaa gcagcatgtc tgaataccct tgacgttttc acagccttga    2820
tgtttccgca gcctgcacct catcgagtcg cgagtgcaag cccgataccc tgcggcctcg    2880
gcccgttttc cagccagcca gggtgtagca gcccgcacat cgtagagtag cagcatggtg    2940
ggtttggctc gggcgaagca cctcgccagc gggaacttct tgaggcttaa tctatgcagg    3000
ggtgcagagg aatgccacat tgaatgtcat cacataagat tgcttatgaa aggcagcttt    3060
cgtgaaccgc tttcagcgca atggtgcagg accacgtgag ggcatgtgac tatgagtggc    3120
acactttgcc aagctgcagg gggtcagcct gctgatcagg aacggctttg tggtttcgga    3180
```

```
cctctggagg actatgttgg tcatcctcgg ggcttgacac gcttacctgg tggtctttgt    3240
aggttgtgca agtttagttt caagttggca ccggcagtgg cccccgtgt atgtgggctg     3300 cacagctgag aagcctggtt ttgtacatgc tggtgcggca ggtatgggca acatgtcaga    3360
gtggcaagca caagtcatgc agggtagacc atcagggtga tatctgcatc gacttcgtgc    3420
ggtctggact gactgaggct tggctttgtg aggcttgcct tgccttttgt gtcatgttcc    3480
agaagaacac agctgctgca aaccttgtgg atgttggtca tgtgatgcct gcacctcgca    3540
ggcgtctcag ctgacacatt atggctattg cggtgactat gcgtctcccg tctttgagcg    3600
cagaacaggg ttccagtgga tcaggaagta tttggtcgga tggtgtggtt gagctcaaga    3660
acgagtggtt tggtcaggtc tagatctcag ctcgggtgag tgcttttcca gaagtagctt    3720
ggttgctggc tgggtgttca ccatagggtt tgtatgtttg tcggcgtccg ttgttccatg    3780
atcatattga agggctgggt tgtaatcaga tgatcatgtt agtgttttg tccgggttga    3840 cttgtggttc gtcacgctag cgtggtgcct agtggttagg gtgtagcgca gcatcgctgc    3900
cgaataatgg acatgatgtc aagcgcctat tcaggaggtg cttgctacat gctgtcgacc    3960
acatcagtgc gcatgggtcc tgcgctattg gctgtgtgct taggctaggt agggttgtgt    4020
aggtgttgac catcagtgga cagcctctgc agtgtgtgtt atgcagagct gctcgtgccc    4080
gatcacaggc atagtgtgag gcttgggatg gcagtgccag ttacacgacg ttgtaaaatg    4140
atttggctc                                                            4149
```

<210> SEQ ID NO 3
<211> LENGTH: 355
<212> TYPE: PRT
<213> ORGANISM: Myrmecia incisa

<400> SEQUENCE: 3

```
Met Glu Leu Ala Ser Ala Lys Ser Ser Phe Leu Ser Ala Trp Gln Leu
1               5                   10                  15

Ala Trp Ala Lys Leu Ser Trp Ala Thr Ser Leu Ile Leu Pro Lys Ala
            20                  25                  30

Ala Ala Ile Tyr Thr Val Gly Ile Tyr Phe Ser Thr Pro Gln Cys Trp
        35                  40                  45

Leu Phe Thr Leu Tyr Leu Leu Phe Cys Glu Asp Val Leu Ile Arg Leu
    50                  55                  60

Leu Val Ala Gly Tyr Leu Ala Trp Ile Phe Val Gly Pro Gly Arg Asp
65                  70                  75                  80

Ala Ala Lys Asn Val Thr Trp Arg Pro Tyr Met Arg Arg Trp Gly Leu
                85                  90                  95

Trp Asn Tyr Leu Ala Ala Tyr Phe Arg Ala Glu Leu Val Lys Thr Ala
            100                 105                 110

Glu Leu Asp Pro Ser Lys Ser Tyr Leu Phe Gly Val His Pro His Gly
        115                 120                 125

Val Leu Thr Met Ala Ser Trp Ile Asn Phe Ser Thr Glu Ser Thr Gly
    130                 135                 140

Phe Ser Asp Lys Phe Pro Gly Ile Glu Met His Val Gly Thr Leu Asn
145                 150                 155                 160

Trp Asn Phe Val Thr Pro Ile Ala Arg Glu Phe Leu Met His Gly
                165                 170                 175

Ala Cys Asp Val Thr Arg Asp Thr Leu Cys Ala Leu Leu Ser Arg Pro
            180                 185                 190

Gly Arg Ala Val Met Val Ala Ile Gly Gly Ala Ala Glu Ala Leu His
```

```
        195                 200                 205
Ala Phe Pro Gly Thr Tyr Asp Leu Val Leu Ala Lys Arg Lys Gly Phe
    210                 215                 220

Val Lys Val Ala Met Met Thr Gly Ala Ser Leu Val Pro Val Leu Cys
225                 230                 235                 240

Phe Gly Glu Asn Glu Val Met Thr Thr Val Lys Val Glu His Gly Ser
                245                 250                 255

Phe Thr His Lys Leu Gln Arg Phe Leu Lys Gly Ile Val Gly Phe Thr
            260                 265                 270

Ile Pro Val Cys Tyr Gly Arg Gly Leu Phe Gly Ile Arg Tyr Gly Ile
        275                 280                 285

Leu Pro Asn Pro Val Arg His Val Thr Val Val Gly Ala Pro Ile Asp
    290                 295                 300

Ile Pro Lys Phe Thr Gly Asp Leu His Ser Glu Gly Gln Ala Ala
305                 310                 315                 320

Val Asn Arg Ala His Ala Lys Tyr Ile Ala Ala Leu Gln Ala Leu Trp
                325                 330                 335

Glu Gln His Lys Asp Gln Tyr Ala Lys Gln Arg Arg Ser Ser Leu His
            340                 345                 350

Ile Ile Glu
        355

<210> SEQ ID NO 4
<211> LENGTH: 25
<212> TYPE: DNA
<213> ORGANISM: Artificial sequence
<220> FEATURE:
<223> OTHER INFORMATION: PCR Primer

<400> SEQUENCE: 4
aggtcgcctg tgaacttggg gatgt                                         25

<210> SEQ ID NO 5
<211> LENGTH: 25
<212> TYPE: DNA
<213> ORGANISM: Artificial sequence
<220> FEATURE:
<223> OTHER INFORMATION: PCR Primer

<400> SEQUENCE: 5
acggtgacat ggcgcacagg gttgg                                         25

<210> SEQ ID NO 6
<211> LENGTH: 24
<212> TYPE: DNA
<213> ORGANISM: Artificial sequence
<220> FEATURE:
<223> OTHER INFORMATION: PCR Primer

<400> SEQUENCE: 6
cagttacaaa tcgcgttctg ctta                                          24

<210> SEQ ID NO 7
<211> LENGTH: 24
<212> TYPE: DNA
<213> ORGANISM: Artificial sequence
<220> FEATURE:
<223> OTHER INFORMATION: PCR Primer

<400> SEQUENCE: 7
tccccagtca agagtgtgct actc                                          24
```

```
<210> SEQ ID NO 8
<211> LENGTH: 26
<212> TYPE: DNA
<213> ORGANISM: Artificial sequence
<220> FEATURE:
<223> OTHER INFORMATION: PCR Primer

<400> SEQUENCE: 8
gaattcaaaa tggagctggc ctcagc                                          26

<210> SEQ ID NO 9
<211> LENGTH: 24
<212> TYPE: DNA
<213> ORGANISM: Artificial sequence
<220> FEATURE:
<223> OTHER INFORMATION: PCR Primer

<400> SEQUENCE: 9
tctagactac tcgatgatgt gcag                                            24

<210> SEQ ID NO 10
<211> LENGTH: 24
<212> TYPE: DNA
<213> ORGANISM: Artificial sequence
<220> FEATURE:
<223> OTHER INFORMATION: PCR Primer

<400> SEQUENCE: 10
gagcggataa caatttcaca cagg                                            24

<210> SEQ ID NO 11
<211> LENGTH: 24
<212> TYPE: DNA
<213> ORGANISM: Artificial sequence
<220> FEATURE:
<223> OTHER INFORMATION: PCR Primer

<400> SEQUENCE: 11
cgccagggtt ttcccagtca cgac                                            24

<210> SEQ ID NO 12
<211> LENGTH: 156
<212> TYPE: DNA
<213> ORGANISM: Artificial sequence
<220> FEATURE:
<223> OTHER INFORMATION: Cloning Site

<400> SEQUENCE: 12
gagcggataa caatttcaca caggaaacag ctatgaccat gattacgcca agcttgcatg     60
cctgcaggtc gacgatatct ctagaggatc cccgggtacc gagctcgaat tcactggccg    120
tcgttttaca acgtcgtgac tgggaaaacc ctggcg                              156
```